United States Patent
Rudnick

[11] Patent Number: 5,780,402
[45] Date of Patent: Jul. 14, 1998

[54] ALKYLATED THIOPHENOL LUBRICANTS

[76] Inventor: Leslie R. Rudnick, 5 Winthrop Rd., Lawrenceville, N.J. 08648

[21] Appl. No.: 748,730

[22] Filed: Aug. 22, 1991

[51] Int. Cl.$^6$ .............. C10M 135/28; C10M 105/72; C07C 319/20; C07C 2/66
[52] U.S. Cl. .............................. 508/573; 568/68
[58] Field of Search ................... 252/45; 568/68; 508/573

[56] References Cited

U.S. PATENT DOCUMENTS

| | | | |
|---|---|---|---|
| 2,402,686 | 6/1946 | Signaigo | 568/68 |
| 2,422,275 | 6/1947 | Winning | 252/45 |
| 2,451,037 | 10/1948 | McCleary | 252/45 |
| 3,084,196 | 4/1963 | Laufer | 568/68 |
| 3,480,580 | 11/1969 | Joyner et al. | 260/29.6 |
| 4,794,205 | 12/1988 | Aslam | 568/68 |
| 5,004,841 | 4/1991 | Lee | 568/68 |
| 5,171,915 | 12/1992 | Forbus et al. | 568/68 |

*Primary Examiner*—Jerry D. Johnson

[57] ABSTRACT

Novel alkylated thiophenols are high temperature stable lubricant fluids having low temperature properties and excellent load-carrying properties and additive solubility.

7 Claims, No Drawings

ALKYLATED THIOPHENOL LUBRICANTS

CROSS REFERENCE TO RELATED APPLICATIONS

This application is related to Ser. No. 07/637,425 filed on Jan. 4, 1991; application Ser. No. 07/639,861 filed on Jan. 11, 1991; Ser. No. 07/686,454 filed on Apr. 17, 1991; Ser. No. 07/686,453 filed on Apr. 17, 1991; Ser. No. 07/686,452 filed on Apr. 17, 1991; application Ser. No. 07/701,900 filed on May 17, 1991; Ser. No. 07/705,997 filed on May 28, 1991.

BACKGROUND OF THE INVENTION

1. Field of the Invention

This invention is directed to improved lubricant compositions comprising alkylated thiophenol lubricant fluids alone or in combination with synthetic or mineral oils, and to mineral or synthetic lubricant oil compositions containing minor amounts of said alkylated thiophenols as multifunctional additives therefor.

2. Description of Related Art

Polyphenyl ethers are known and have been used as lubricants in special applications. Polyphenyl ethers suffer from very high cost due to difficult synthesis and have poor low-temperature properties.

Incorporation of linear alkyl groups into diphenyl ether eliminates both of the above problems and provides a novel, relatively inexpensive lubricant having excellent low-temperature properties. The use of these adducts as a lubricant or lubricant additive in either mineral or synthetic lubricant has been recently disclosed in copending applications.

With respect to alkylated thiophenols, U.S. Pat. No. 4,948,827 discloses the use of methyl-2-tertiary buty-5-thiophenol as a stabilizer for plastic films and as a chain transfer agent.

We now disclose the preparation and use of alkylated thiophenols as a new class of lubricating fluids. These have the advantages of alkylated diphenyl sulfides in that the polar sulfur provides excellent additive solubility and good lubricating properties.

BRIEF SUMMARY OF THE INVENTION

This application is directed to novel lubricant and fuel compositions comprising from about less than one percent to about 100% of alkylated thiophenols as disclosed herein and to mineral and synthetic lubricants and fuels containing minor proportions of the disclosed thiophenols as multifunctional additives.

This invention is more particularly directed to alkylated thiophenols produced by the reaction of diphenyl disulfides with olefins. This reaction avoids the use of the more volatile thiophenol as a reactant and clearly produces monoalkylated thiophenol by cleavage, in situ, of the disulfide linkage.

The low temperature properties of these alkylated thiophenols is excellent and believed to be improved over materials of branched structure due to the facility for carbon-carbon bond breaking in the latter materials.

The use of these adducts as a lubricant or lubricant additive in either mineral or synthetic lubricants is unique and provides improved properties and performance benefits due to inherent synergism. It is expected that the performance benefits will include antifatigue, antispalling, antistaining, antisquawking, improved additive solubility, improved load carrying/bearing, extreme pressure, improved thermal and oxidative stability, friction reducing, antiwear, anticorrosion, cleanliness improving, low- and high-temperature antioxidant, demulsifying, emulsifying and detergency properties.

It is therefore an object of this invention to provide novel lubricant compositions comprising the alkylated thiophenols in accordance with the invention and novel lubricant and fuel compositions containing minor proportions of said thiophenols as additives.

DESCRIPTION OF THE PREFERRED EMBODIMENTS

Low viscosity fluids which provide good oxidation control and provide excellent antiwear and load-carrying properties are unique. The process of generating these new base stocks does not involve direct alkylation of thiophenol.

The products obtained from the reaction of a linear olefin and diphenyl disulfide in the presence of specific zeolite catalysts are unique not only in composition and structure but in utility. Part of the uniqueness may be derived from the specific reaction over zeolite catalyst; generally, they have a higher VI at a given viscosity. The incorporation of various alkyl groups into the diphenyl disulfide structure provides compositions of different viscosity and low temperature viscometrics.

These unique lubricants exhibit beneficial properties from the unique reaction of olefin with the thiophenol structure in such a way as to remain predominantly linear. This is a direct result of the catalytic reaction. This combination provides for the novel structural class disclosed here. The use of these compositions of matter as either functionalized alkyl thiophenol lubricant fluids or lubricant additives is believed to be novel.

Broadly, the novel class of hydrocarbon products of the present invention can be characterized as adducts of a hydrocarbyl substituent, which can contain one or more olefin groups, and a diphenyl disulfide. The hydrocarbyl group can contain from $C_3$–$C_{500}$, preferably $C_6$–$C_{50}$ and most preferably $C_8$–$C_{18}$. The hydrocarbyl group can optionally contain S, N, O, P, and/or F. The hydrocarbyl can be alkyl, alkenyl, alkynyl, arylalkyl, aliphatic, cyclic, linear or branched. Substitution can be on one or more positions of the aromatic rings, with alkylation on either or both rings.

The preparation of these novel compositions may be by means of a thermal or catalytic addition reaction. The exact mechanism of the reaction is not important to the purposes of this invention, so long as the hydrocarbyl group becomes attached to the diphenyl disulfides or thiophenols described herein.

One preferred method of reaction between the hydrocarbyl group and the diphenyl disulfide is the combination of these reactants in the presence of specific zeolite catalysts. Non-limiting examples are Octacat USY, ZSM-5, ZSM-12 and MCM-22. This reaction is affected at temperatures ranging from ambient to 350° C., preferably from 100°–250° C. and most preferably from 180°–240° C. over a period required to produce desired conversion of reactants to product. Optionally, the reaction can be performed in a batch or semi-batch mode by continuous or partial addition of the catalyst or hydrocarbyl group to the diphenyl disulfide. Catalyst can be used at levels ranging from 1 gram/mole of aromatic to 50 grams/mole of aromatic, preferably 5 gram/mole of aromatic to 50 gram/mole of aromatic, and most preferably from 10–30 gram/mole of aromatic.

Optionally, the products of this invention can be prepared by reaction of the hydrocarbyl group with diphenyl disulfide in the presence of AlCl$_3$ and other proton or Lewis acids as described in G. A. Olah's "Friedel-Crafts and Related Reactions", Vol. 1, 1963, Interscience Publishers.

The hydrocarbon compositions of the present invention relate to improved thermally and oxidatively stable fluids. These may be used optionally as liquid lubricants or in liquid lubricant compositions, and as solid lubricants or in solid lubricant compositions including greases, such as polyurea, lithium carboxylate or clay-thickened greases.

These hydrocarbon compositions may also be used in combination with additives, for example, antioxidants, EP/antiwear agents, inhibitors, detergents and dispersants, and viscosity index improvers. Non-limiting examples of antioxidants include phenols which can be hindered and aromatic amines.

Non-limiting examples of EP/antiwear additives include zinc phosphorodithioates, sulfurized esters, sulfurized olefins, phosphonates, phosphates, phosphorothionates, etc. Non-limiting examples of inhibitors include DMTD, phenothiazine, etc. Non-limiting examples of detergents and dispersants include sulfonates, phenates, and polymeric succinimides. These can be either metallic or non-metallic. Metallic detergents can be calcium or magnesium derived and can be neutral or over based.

The hydrocarbon compositions of this invention can be used alone or in combination with other synthetic and/or mineral oil fluids.

Fuel compositions are also contemplated for use herein, these include both hydrocarbon fuels, including gasoline, naphtha and diesel fuels or alcoholic fuels or mixtures of alcoholic and hydrocarbon fuels. Fuel compositions can contain 10 to 1000 pounds of the alkylated thiophenols as additive per 1000 barrels of fuel or more preferably 25 to 250 pounds per 1000 barrels of fuel.

In general, the production of alkylated thiophenols is favored by the use of zeolite catalysts such as zeolite beta or zeolite Y, preferably USY, of controlled acidity, preferably with an alpha value below about 200, and for best results, below 100, e.g., about 25–50.

The alpha value of the zeolite is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 sec −1). The alpha test is described in U.S. Pat. No. 3,354,078 and in J. Catalysis, 4, 527 (1965); 6, 278 (1966); and 61, 395 (1980), to which reference is made for a description of the test. The experimental conditions of the test used to determine the alpha values referred to in this specification include a constant temperature of 538° C. and a variable flow rate as described in detail in J. Catalysis, 61, 395 (1980).

When the compositions of the present invention are used alone or in combination with other synthetic and/or mineral oil fluids, the below described oils of lubricating viscosity may be used.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. to about 6000 SSU at 100° F. and preferably, from about 50 to about 250 SSU at 210° F. These oils may have viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for foaming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

EXAMPLES

The following examples are exemplary only and are not intended to limit the invention.

Example 1

To a vigorously stirred mixture of diphenyl disulfide (109.2 g, 0.5 mole) and 1-tetradecene (196 g, 1.0 mole) in a flask fitted with thermocouple and reflux condenser was added 15 g of FCC Octacat USY catalyst. The mixture was heated to 200° C. with stirring for six hours. After cooling to room temperature, the mixture was filtered to remove catalyst and vacuum distilled to 170° C. at 0.5–1.5 mmHg to remove unreacted starting materials.

Example 2

Using the procedure in Example 1, diphenyl disulfide (109.2 g, 0.5 mole) and 1-tetradecene (196 g, 1.0 mole) were reacted using 30 grams of FCC Octacat USY catalyst.

Example 3

Using the procedure in Example 1, diphenyl disulfide (109.2 g, 0.5 mole) and 1-dodecene (168.32 g, 1.1 moles) were reacted using 15 grams of FCC Octacat USY catalyst.

Example 4

Using the procedure in Example 1, diphenyl disulfide (109.2 g, 0.5 mole) and 1-hexadecene (224 g, 1.0 mole) were reacted using 15 grams of FCC Octacat USY catalyst.

Example 5

Using the procedure in Example 1, diphenyl disulfide (109.2 g, 0.5 mole) and 1-octadecene (252.5 g, 1.0 mole) were reacted using 15 grams of FCC Octacat USY catalyst.

Example 6

To a stirred mixture of 1-octene (424.2 g, 2 moles), and diphenyl disulfide, 109.2 g (0.5 mole), was added 2.0 grams of anhydrous $AlCl_3$, and heated at reflux for six hours. The mixture was cooled, washed to remove inorganic materials, dried over anhydrous $MgSO_4$. Gas chromatographic analysis showed essentially complete reaction of starting material. Color of this material was >5 whereas the product of Example 1 was <2.0.

Example 7

Using the procedure in Example 6, 1-decene, 140.27 g (1 mole) and diphenyl disulfide (109.2 g, 0.5 mole) were reacted with $AlCl_3$ (2 grams) at reflux for six hours. Vacuum distillation of the washed organic mixture to 170° C. at 0.5–1.5 mmHg resulted in the desired hydrocarbyl thiophenol product.

Typical properties of an exemplary hydrocarbyl thiophenol are shown in Table 1.

TABLE 1

| Hydrocarbyl | $C_{16}$ |
|---|---|
| KV @ 100° C., cst | 2.9 |
| VI | 113 |
| Pour Point (°C.) | −31 |

Hexadecene alkylated thiophenol was compared to polyolefin base stock in a Four-Ball Wear test. The results show that at higher load, the alkyl thiophenol produced less wear than the other base stock, with improved coefficient of friction (f). The alkyl thiophenol also had a significantly higher load wear index and weld load.

In the Four-Ball Wear Test, three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 52100 steel for thirty minutes under 30 kg load at 1800 rpm and 200° F. If additional information is desired, consult test method ASTM D2266 and/or U.S. Pat. No. 4,761,482.

K (as reported in Table 2) the wear coefficient is calculated from the wear volume, V, of the stationary ball. The wear volume is calculated from the wear scar diameter D in mm as follows:

$$V = [15.5\ D^3 - 0.001033 L] D \times 10^3\ mm^3$$

where L is the machine load in kg. This equation considers the elastic deformation of the steel balls.

Wear Coefficient K

Dimensionless K is defined as K=VH dN
where

V=wear volume, mm3

H=hardness 9725 kg/mm2 for 52100 steel d=(23.3 mm/rev) (RPH×Time)

N=(0.408) (Load in kg)

f=the Coefficient of Friction

LNS=Last Non Seizure Load

LWI=Load Wear Index

In the Four Ball EP Test the weld load, in KG force, is determined by the ASTM D-2596 Four-Ball EP test in which a steel ball, under a constant force or load, is rotated at a speed of 1770 RPM against three other balls held in a stationary position in the form of a cradle. The temperature is maintained at 100° C. and the rotating ball is subjected to successively higher loads for 10 seconds each until the four balls weld together. The results are summarized in Table 3 below.

TABLE 2

Four-Ball Wear Test Results
(1800 RPM/200° F./40 Kg/30 min)

|  | K | f |
|---|---|---|
| $C_{16}$-thiophenol | 12.3 | 0.11 |
| CSL* | 402 | 0.076 |

TABLE 3

Four-Ball EP Test Results (100° C.)

|  | LNS | LWI | Weld |
|---|---|---|---|
| $C_{16}$-thiophenol | 32 | 28 | 250 |
| CSL* | 32 | 14.6 | 126 |

*CSL = Commercial Synthetic Lubricant

The Four-Ball Wear Test and Four-Ball EP Test results demonstrate the excellent antiwear and EP properties of the compositions in accordance with the invention.

Although the present invention has been described with preferred embodiments, it is to be understood that modifications and variations may be resorted to, without departing from the spirit and scope of this invention, as those skilled in the art will readily understand. Such variations and modifications are considered within the purview and scope of the appended claims.

I claim:

1. A process for the preparation of a high-temperature stable lubricant fluid or lubricant additive comprising reacting (1) an olefinic hydrocarbon containing from 3 to about 500 carbons and optionally containing S, N, O, P, F, and (2) a diphenyl disulfide in the presence of a zeolite catalyst thereby forming a monoalkylated thiophenol wherein the reaction temperature varies from ambient to about 350° C., the molar ratio of olefinic hydrocarbon to diphenyl disulfide varies from 1:1 to about 1 0:1 and the amount of catalyst varies from 5 to about 100 grams of catalyst to about 1 mole of diphenyl disulfide.

2. The process of claim 1 wherein the zeolite catalyst is USY, ZSM-12, or MCM-22.

3. The process of claim 2 wherein the zeolite catalyst is USY.

4. The process of claim 3 wherein the reactants are 1-tetradecene and diphenyl disulfide and the zeolite catalyst is USY.

5. The process of claim 3 wherein the reactants are 1-dodecene and diphenyl disulfide and the zeolite catalyst is USY.

6. The process of claim 3 wherein the reactants are 1-hexadecene and diphenyl disulfide and the zeolite catalyst is USY.

7. The process of claim 3 wherein the reactants are 1-octadecene and diphenyl disulfide and the zeolite catalyst is USY.

* * * * *

UNITED STATES PATENT AND TRADEMARK OFFICE
CERTIFICATE OF CORRECTION

PATENT NO. : 5,780,402
DATED : July 14, 1998
INVENTOR(S) : Leslie R. Rudnick

It is certified that error appears in the above-identified patent and that said Letters Patent is hereby corrected as shown below:

Title page, item [73];

Add Assignee: "Mobil Oil Corporation, Fairfax, VA", and --Attorney, Agent, or Firm --Malcolm Keen--.

Signed and Sealed this

Twentieth Day of October, 1998

Attest:

BRUCE LEHMAN

Attesting Officer

Commissioner of Patents and Trademarks